United States Patent [19]

Halbritter et al.

[11] 4,072,717

[45] Feb. 7, 1978

[54] MANUFACTURE OF FORMALDEHYDE

[75] Inventors: Guenter Halbritter, Germersheim; Wolfgang Muehlthaler, Hemsbach; Heinrich Sperber, Ludwigshafen; Hans Diem, Ludwigshafen; Christian Dudeck, Ludwigshafen; Gunter Lehmann, Ludwigshafen, all of Germany

[73] Assignee: BASF Aktiengesellschaft, Ludwigshafen (Rhine), Germany

[21] Appl. No.: 606,773

[22] Filed: Aug. 22, 1975

[30] Foreign Application Priority Data

Sept. 4, 1974 Germany ............................ 2442231

[51] Int. Cl.$^2$ ............................................. C07C 45/16
[52] U.S. Cl. ................................................ 260/603 C
[58] Field of Search ............ 260/603 HF, 603, 603 C

[56] References Cited

U.S. PATENT DOCUMENTS

| 2,436,287 | 2/1948 | Brondyke ...................... 260/603 HF |
| 2,462,413 | 2/1949 | Meath ........................... 260/603 HF |
| 3,728,398 | 4/1973 | Maux ............................ 260/603 HF |
| 3,928,461 | 12/1975 | Diem et al. ................... 260/603 HF |

*Primary Examiner*—James O. Thomas, Jr.
*Assistant Examiner*—W. B. Lone
*Attorney, Agent, or Firm*—Keil, Thompson & Shurtleff

[57] ABSTRACT

Formaldehyde is prepared by oxidative dehydrogenation of methanol in the presence of a silver catalyst, specific amounts of steam and specific amounts of an off-gas, of a specific composition, taken from the manufacture of formaldehyde. The reaction is started at a lower throughput of methanol and at a lower temperature. The formaldehyde obtainable by the process is a disinfectant, tanning agent and reducing agent, and a starting material for the manufacture of synthetic resins, adhesives and plastics.

12 Claims, No Drawings

MANUFACTURE OF FORMALDEHYDE

The present invention relates to a process for the manufacture of formaldehyde by oxidative dehydrogenation of methanol in the presence of a silver catalyst, specific amounts of steam and specific amounts of an off-gas, of a specific composition, taken from the manufacture of formaldehyde, wherein the reaction is started at a lower throughput of methanol and a lower temperature.

Belgian Pat. No. 683,130 discloses the manufacture of a concentrated aqueous formaldehyde solution by passing an anhydrous methanol-air mixture over a silver catalyst in the presence of inert gases and absorbing the resulting formaldehyde in water. This process gives yields of formaldehyde of from 80 to 86% of theory. The off-gas obtained after isolating the formaldehyde is recycled to the reaction, is appropriate. The Examples quote a minimum methanol content of 1.8% in the formaldehyde solutions obtained. The description (page 3) discloses passing the starting mixture over a catalyst heated to from 600° to 660° C. Example 4 discloses starting the reaction over the catalyst without addition of off-gas; when sufficient amounts of off-gas have been formed by the reaction and subsequent absorption stage, a part of this off-gas is recycled to the starting mixture. All the Examples show that the reaction is carried out only with small amounts of the starting materials. Since the gaseous starting mixture does not introduce any steam into the reaction, absorption results in formaldehyde solutions of up to 60 percent strength by weight.

German Published Application No. 1,903,197 discloses that the oxidation of methanol can also be carried out in the presence of from 0.2 to 1 mole of water and with from 1 to 1.65 moles of the off-gas obtained from the reaction after the absorption stage, per mole of methanol. According to the Examples, yields of 88.6% are obtained, corresponding to a 50 percent strength by weight formaldehyde solution containing 0.7% by weight of methanol. If the reaction is carried out without added water, a 55 percent strength by weight solution containing 1.7% by weight of methanol is obtained, the yield being 84.8% of theory. If the reaction is carried out without added inert gas or off-gas, the yield is admittedly 88.6%, as disclosed by the German Published Application, but solutions of only 33 percent strength by weight are obtained, containing 0.65% by weight of methanol. In this process also, as disclosed by the Examples, the off-gas and the starting mixture are passed over a catalyst heated to 650° C. The off-gas, which as a rule is free from formaldehyde, is in each case taken from the actual reaction (page 1, penultimate paragraph, and the Examples); since all the Examples are carried out with only small amounts of starting materials, sufficient amounts of formaldehyde-free off-gas thus obtained can be recycled starting only a short time after the start of the reaction.

German Published Application No. 2,022,818 discloses that starting mixtures which contain off-gas and steam will only give good yields of end product coupled with a lower methanol content and more concentrated formaldehyde solutions if the off-gas which here again originates from the actual reaction is purified by means of basic compounds and/or oxidizing agents before being recycled. In this process, again, the starting mixture is passed, from the very start, over a catalyst heated to not less than 550° C (page 4), but as a rule 650° (as disclosed by all the Examples).

Japanese Pat. Application No. 21,081/73 discloses first reacting a mixture of methanol vapor and air, in the presence of an inert gas which is practically free from carbon dioxide and carbon monoxide, over a catalyst heated to not less than 600° C, and progressively replacing the inert gas, over a prolonged duration of reaction, by the off-gas formed in the reaction. In this process, the reaction is again carried out on a laboratory scale, as is disclosed by the Examples. The patent application expressly emphasizes that the starting mixture is passed, from the very start, over a catalyst heated to high temperatures and that the off-gas formed in the formaldehyde reaction cannot be used immediately after the start of the reaction; the description discloses that there are no adverse effects if the off-gas is only added at a later stage. A disadvantage is the formation of a large amount of carbon, particularly in the case of a reaction using substantial amounts of starting materials, since this formation of carbon in particular does not permit reliable continuous operation.

If the processes described in German Published Application No. 1,903,197, the Belgian Patent and the Japanese Patent Application are carried out on a commercial scale, e.g. with from 50 to 200 kg/hour of methanol, and in particular on an industrial scale, e.g. with from 0.2 to 20 tonnes of methanol per hour, the yields found are as a rule less than 88% of theory of formaldehyde, and the formaldehyde solutions obtained are of 50 percent strength by weight and contain up to 2.25% of methanol. Because of the large amounts of the reactants the off-gas is only recycled after at least 3 hours and as a rule after at least 24 hours.

It is an object of the present invention to provide a process for the manufacture of formaldehyde, whereby better overall results in respect of high concentration of the formaldehyde solution produced, better yield of end produce, high conversion and low content of methanol and formic acid in the solution are obtained, more simply and more economically.

We have found that this object is achieved and that formaldehyde is obtained in an advantageous manner by oxidative dehydrogenation of methanol in the presence of a silver catalyst at elevated temperatures, if (a) a gaseous starting mixture of methanol and steam, containing from 0.1 to 0.7 mole of water per mole of methanol, is passed through the catalyst, heated to from 250° to 450° C, at a throughput of from 0.04 to 1.0 tonne of methanol per square meter of catalyst bed cross-section per hour, thereafter (b) air corresponding to from 0.3 to 0.6 mole of oxygen per mole of methanol is added to the starting mixture at the above temperature, and the reaction over the catalyst is started, (c) at a point in time within the period from before the reaction to 0.5 hour after the start of the reaction, an off-gas taken from the manufacture of formaldehyde by oxidative dehydrogenation of methanol and containing from 0.25 to 1.0 percent by volume of carbon monoxide, from 3.5 to 10.0 percent by volume of carbon dioxide, from 10 to 25 percent by volume of hydrogen and from 0.02 to 0.1 percent by volume of formaldehyde vapor, is admixed to the starting mixture, in amounts of from 90 to 3,500% by weight of off-gas, based on methanol, thereafter (d) the throughput of gaseous mixture fed to the catalyst, and the reaction temperature, are both increased and finally (e) the reaction is carried out at from 550° to 800° C, at a throughput of from 1 to 3 tonnes of methanol per square meter of catalyst bed cross-section per hour, using a ratio of from 0.2 to 0.7 mole of steam and from 0.3 to 0.8 mole of oxygen per mole of methanol, and from 90 to 180% by weight of off-gas, based on methanol.

Compared to the conventional processes, the process of the invention gives better overall results in respect of high concentration of the formaldehyde solution produced, better yield of end product, high conversion and low content of methanol and formic acid in the solution, more simply and economically, particularly on a commercial scale. Using the new process, the methanol gives, in a single pass, yields of formaldehyde of from 89 to 92% of the theoretical yield. The aqueous solution obtained after absorption of the formaldehyde from the gases containing formaldehyde, contain from 50 to about 60% by weight, preferably from 50 to 55% by weight, of formaldehyde, and only from 0.5 to 1.1% by weight of methanol. The formaldehyde solution obtained has a low formic acid content, as a rule less than 0.015% by weight, based on a 50 percent strength by weight formaldehyde solution. The process of the invention permits more trouble-free running, with higher and more constant conversion of the starting mixture, longer working life of the catalyst and large cross-section of the catalyst bed, particularly on an industrial scale. Special measures to avoid temperature fluctuations in the catalyst are superfluous. These advantageous results are achieved together with a longer catalyst life and fluctuations in results are therefore avoided over prolonged periods. Additional washing of the off-gas and hence consumption of chemicals, is avoided, in contrast to German Published Application No. 2,022,818. Nor is it necessary to use additional inert gas.

The results are surprising in view of the art, since the reaction starts at a lower temperature and the off-gas, which may initially come from another formaldehyde manufacturing installation, is suitably added beforehand to the starting mixture from the very start of the reaction. Furthermore the off-gas contains higher amounts of carbon dioxide and carbon monoxide and of formaldehyde, contrary to the disclosure of German Published Application No. 1,903,197 and of Japanese Patent Application No. 21,081/73.

Suitable starting materials for the process are pure methanol or technical methanol, advantageously in the form of mixtures with water; the methanol concentration of such aqueous mixtures may suitably be from 50 to 95% by weight, preferably from 70 to 85% by weight. Crude methanol, which as a rule is purified by the processes disclosed in German Printed Application No. 1,277,834, German Pat. No. 1,136,318 and German Pat. No. 1,235,881, by removing a lower-boiling fraction and by treatment with oxidizing agents and/or alkalis, may also be used. The methanol vapor and steam may be generated separately and mixed with air, but it is more advantageous to vaporize a suitable aqueous solution of methanol and admix air to the vapor mixture; suitably, the air is admixed during the actual vaporization, by passing the gas through the methanol solution.

The catalysts which may be used for the process of the invention are the silver catalysts conventionally used for the manufacture of formaldehyde, e.g. those described in German Printed Application No. 1,231,229 and Ullmanns Encyklopedie der technischen Chemie, volume 7, pages 659 et seq. Preferably, two-layer and multi-layer silver catalysts are used, e.g. those described in German Printed Application No. 1,294,360 and in German Patent Application No. P 19 03 197.1. Regarding the manufacture of the catalyst and the method of carrying out the reaction with these catalysts, reference may be made to the said publications. In a preferred embodiment, the reaction is carried out with a total catalyst bed thickness of from 15 to 35 mm and with 3 or more layers of silver crystals, of which some of the layers contain from 72.5 to 89% by weight of the catalyst of particle size from 1 to 2.5 mm, some of the layers contain from 2.5 to 7.5% by weight of the catalyst of particle size from 0.75 to 1 mm, and the remainder of the layers contain from 8.5 to 20% by weight of the catalyst of particle size from 0.2 to 0.75 mm. Preferred catalyst are described in German Patent Application No. P 23 22 757. The ratio of the diameter to the thickness of the catalyst bed, which preferably consists of two or more layers of different particle size, is at least 25, preferably from 40 to 200, and especially from 60 to 100. In general, the diameter is at least 500 mm, preferably from 1,500 to 4,000 mm and especially from 1,700 to 3,000 mm.

The use of an inert gas is unnecessary and, at reaction temperatures above 550° C, and especially 600° C, is even undesirable. If required, the catalyst can be heated with hot inert gases, suitably nitrogen or combustion gases which contain little carbon and no catalyst poisons, e.g. from 400° to 1,300° C and preferably from 600° to 800° C. This embodiment has advantages over the use of indirect heating, e.g. electrical heating, especially on an industrial scale, where large amounts of catalyst are concerned. In contrast to the teaching of the Japanese Patent Application, it is possible to use combustion gases containing carbon monoxide and carbon dioxide, e.g. containing up to 8% by weight of $CO_2$ and up to 10–15% by weight of CO. For example, the catalyst can be heated to the low temperature stage a) by means of the inert gas, and the heating with the inert gas can then be terminated and the reaction carried out. It is also possible to continue the introduction of the hot inert gas whilst passing in methanol and steam and terminate the heating after the air has been introduced. Suitably, the heated is terminated at or after the start of the reaction. Not later than on reaching a catalyst temperature of 450° C, the introduction of inert gas is terminated.

As a rule, the catalyst is heated, before the start of stage (a) of the process, to a temperature of from 250° to 400° C, preferably from 280° to 350° C, and the starting mixture is then passed through the catalyst in an amount of from 0.1 to 0.7 mole, preferably from 0.3 to 0.5 mole, of steam per mole of methanol vapor, the throughput being from 0.04 to 1.0 tonne, preferably from 0.05 to 0.7 tonne, of methanol per square meter of catalyst bed cross-section per hour. The starting mixture, in the vapor state, is suitably at from 60° to 85° C, preferably from 65° to 75° C, before entering the catalyst.

The start of the exothermic reaction is suitably ascertained by adding air to the starting mixture and examining the temperature change in the catalyst. If the reaction starts, an immediate rise in temperature is observed; if it does not start, the temperature drops as a result of the introduction of the cold air. A suitable method of measuring the temperature in the catalyst is by means of thermocouples. From the start of the reaction, the air is in general fed continuously into the starting mixture which is in the vapor state, if appropriate by passing the air into the bottom of the vaporizer column. Suitable amounts of oxygen, in the form of air, are from 0.3 to 0.6 mole, preferably from 0.35 to 0.45 mole, per mole of methanol. It is advantageous first to pass the starting mixture through the catalyst for from 0.1 to 120 minutes and then to introduce the air.

Where higher throughputs are concerned, the off-gas used can be off-gas taken from another unit for the manufacture of formaldehyde by oxidative dehydrogenation of methanol, preferably in the presence of a silver catalyst or of a metal oxide, e.g. an iron oxide or molybdenum oxide. Equally, it can be taken from processes using metal oxides on carriers, advantageously on silicate carriers, and/or from processes using the above oxides and additives such as cobalt oxide, nickel oxide, chromium oxide, tungsten oxide, aluminum oxide, phosphorus trioxide or phosphorus pentoxide. Information on processes for the manufacture of formaldehyde may be found in Ullmanns Encyklopedie der technischen Chemie, volume 7, pages 659 et seq. Equally, the off-gas originating from another manufacturing unit can be replaced by the off-gas from the reaction during the course of the latter. In many cases, the off-gas from the reaction according to the invention is used, provided sufficient amounts of off-gas are formed within a short time from the beginning of the reaction. It is possible to recycle the major proportion of the off-gas or, preferably, a minor proportion. The off-gas contains from 0.25 to 1.0, preferably from 0.4 to 0.7, percent by volume of carbon monoxide, from 3.5 to 10, preferably from 4.5 to 7, percent by volume of $CO_2$, from 10 to 25, preferably from 15 to 22, percent by volume of $H_2$, from 0.02 to 0.1, preferably from 0.03 to 0.07, percent by volume of formaldehyde vapor and substantial amounts of nitrogen and small amounts of steam, methanol vapor, argon and other rare gases. The off-gas may be admixed to the starting mixture beforehand or simultaneously with the air, and the two gas mixtures may be fed in conjointly or separately. The off-gas may be admixed at the high temperature of stage (e) or, suitably, at a lower temperature, preferably at the temperature of stage (b). It must be admixed within 0.5 hour, and preferably within 0.25 hour, from the start of the reaction. Preferably, the off-gas is added at the start of the reaction or within 10, and preferably 5.5, minutes thereof. The off-gas may be fed in separately or via the air feed or via the vaporizer of the methanol-water mixture. Amounts of from 90 to 3,500, preferably from 105 to 3,200, % by weight of off-gas, based on methanol, may be used in stage (c).

After the start of the reaction the temperature is raised rapidly or slowly, suitably in the course of from 10 to 150 minutes, intermittently or preferably continuously, and advantageously at the rate of from 1° to 30° C per minute, to from 550° to 800° C, preferably from 650° to 800° C, and especially from 650° to 730° C. The temperature may be raised by indirect heating and/or, suitably, by a corresponding increase in the amount of air. As the latter is increased, so the throughput of gaseous total mixture also rises. Preferably, the amounts of methanol vapor, steam, air and off-gas passed through are increased progressively until the final temperature is reached. However, it is also possible only to increase the feed of these 4 components, and hence the throughput of methanol, after the final temperature has been reached. It is also possible to vary the addition of each individual component separately in respect of time and/or amount, e.g. to admix the off-gas entirely or partly at the final temperature.

When the final temperature has been reached, the ultimate reaction conditions may be set up immediately or within a period of up to 65 hours. At a throughput of from 1 to 3 tonnes, preferably from 1.25 to 2.1 tonnes, of methanol per square meter of catalyst bed cross-section per hour, from 0.2 to 0.7 mole, preferably from 0.3 to 0.5 mole, of steam and from 0.3 to 0.8, preferably from 0.4 to 0.6, mole of oxygen in the form of air are used per mole of methanol, and from 90 to 180% by weight, preferably from 105 to 158% by weight, based on methanol, of off-gas are used. The reaction temperature and conditions are then suitably maintained at these values for the remainder of the reaction time when the reaction is carried out continuously. It is advantageous to cool the reaction gases which leave the catalyst zone in the second stage, e.g. to temperatures of 350° C, within s short time, e.g. in less than 1/10 second. The cooled gas mixture is then preferably fed to an absorption tower in which the formaldehyde is washed out of the gas mixture with water, advantageously in counter-current. Advantageously, a part of the remaining off-gas is then allowed to escape whilst the other part is returned to the reaction cycle. In general, stages a) and b) take place in from 2 to 30 minutes, preferably from 10 to 20 minutes; the catalyst is then heated, suitably in from 10 to 150 minutes, and for the remainder of the reaction time the starting mixture is reacted as in process stage e). In general, the process is carried out at from 0.5 to 2 atmospheres, preferably from 0.8 to 1.8 atmospheres.

Since a silver catalyst is usually very sensitive to fluctuations in throughput, it is surprising that the above method of operation permits reliable, rapid and simple start-up of the catalyst. The formic acid content initially rises to at most 300 ppm and then drops very rapidly to less than 100 ppm.

After the reaction, the gases containing formaldehyde may also be fed to a plurality of absorption units instead of only one. Furthermore, a plurality of vaporizers may be used instead of only one, the vapor mixture from these being combined.

The formaldehyde which can be manufactured by the process of the invention is a disinfectant, tanning agent, reducing agent and valuable starting material for the manufacture of synthetic resins, adhesives and plastics. Its uses are discussed Ullmann, loc. cit., page 670.

The parts in the Examples are by weight and bear the same relation to parts by volume as that of the kilogram to the cubic meter.

EXAMPLE 1

An installation using a methanol vaporizer and a vertical reactor is used. At its top, the reactor is fitted with the inlet for the starting mixture, which is in the vapor state, and with the reactor hood. The catalyst bed is below the reactor top and a cooling zone is provided lower still. The reactor is coupled to an absorption column.

A catalyst comprising 0.187 part of silver crystals of the following composition is introduced into the reactor:

|  | Proportion in the catalyst (% by weight) | Particle size mm |
|---|---|---|
| Layer 1 | 12.9 | 0.4 – 0.75 |
| Layer 2 | 1.2 | 0.2 – 0.4 |
| Layer 3 | 5.3 | 0.75 – 1 |

-continued

| | Proportion in the catalyst (% by weight) | Particle size mm |
|---|---|---|
| Layer 4 | 14.1 | 1 – 1.75 |
| Layer 5 | 66.5 | 1 – 2.5 |

Layer 2 is sprinkled as an annular layer onto layer 3, in the edge zone of the catalyst. The catalyst bed diameter is 200 cm and the internal diameter of the annular layer is 197 cm.

The catalyst is heated to 330° C by passing hot nitrogen through it.

The vapors, at a temperature of 74° C, issuing from a vaporizer and consisting of 0.18 part of methanol and 0.12 part of steam per hour enter the hood of the reactor and flow through the catalyst. The nitrogen feed is discontinued. The throughput is 0.057 tonne of methanol per square meter of catalyst bed cross-section per hour.

0.15 part of air per hour is now passed into the liquid in the vaporizer, whereupon the temperature of the catalyst begins to rise. After 2 minutes, the catalyst temperature is 440° C. After 3 minutes, 0.288 part per hour of an off-gas from the same oxidative dehydrogenation of methanol over a silver catalyst, which gas contains 0.5 percent by volume of carbon monoxide, 4.4 percent by volume of carbon dioxide, 17.7 percent by volume of hydrogen and 0.04 percent by volume of formaldehyde, is fed into the starting mixture in the stream of gas and vapor, upstream from the catalyst.

The amount of air is then increased to 0.313 part per hour in the course of 0.4 hour, during which time, if the pressure is 1.09 bar, the catalyst temperature assumes a value of 700° C.

The throughput is then increased in the course of 61 hours to 2 tonnes of methanol per hour per square meter, at a constant catalyst temperature of 700° C, and at the same time the throughput of steam, air and off-gas is raised gradually in the corresponding ratio; the reaction is then carried out for 120 days at this final level of throughput. The pressure rises, during this time, from 1.21 to 1.54 bars. On reaching the final level of throughput, the amounts per hour are 14.6 parts of air, 1.57 parts of steam, 6.28 parts of methanol and 10.05 parts of off-gas. The reaction mixture is cooled continuously to 150° C and then absorbed, after further cooling, in water in an absorption tower. From the 61st hour onward, 5.218 tonnes per hour of formaldehyde (taken as 100% strength) are obtained in the form of a 50.4 percent strength by weight aqueous solution containing 0.85% by weight of methanol and 0.008% by weight of formic acid. This corresponds to a yield of 89.88% of theory and to 98.6% conversion. The yield of end product and the methanol content of the formaldehyde solution obtained remain constant for 120 days. No cracks form in the catalyst bed.

EXAMPLE 2

An installation using a methanol vaporizer and a vertical reactor is used. At its top, the reactor is fitted with the inlet for the starting mixture, which is in the vapor state, and with the reactor hood. The catalyst bed is below the reactor top and a cooling zone is provided lower still. The reactor is coupled to an absorption column.

A catalyst comprising 0.187 part of silver crystals of the following composition is introduced into the reactor:

| | Proportion in the catalyst (% by weight) | Particle size mm |
|---|---|---|
| Layer 1 | 12.9 | 0.4 – 0.75 |
| Layer 2 | 1.2 | 0.2 – 0.4 |
| Layer 3 | 5.3 | 0.75 – 1 |
| Layer 4 | 14.1 | 1 – 1.75 |
| Layer 5 | 66.5 | 1 – 2.5 |

Layer 2 is sprinkled as an annular layer onto layer 3, in the edge zone of the catalyst. The catalyst bed diameter is 200 cm and the internal diameter of the annular layer is 197 cm.

The catalyst is heated to 330° C by passing hot nitrogen through it.

The vapors, at a temperature of 74° C, issuing from a vaporizer and consisting of 0.18 part of methanol and 0.12 part of steam per hour enter the hood of the reactor and flow through the catalyst. The nitrogen feed is discontinued. The throughput is 0.057 tonne of methanol per square meter of catalyst bed cross-section per hour.

0.15 part of air per hour is now passed into the liquid in the vaporizer, whereupon the temperature of the catalyst begins to rise. After 2 minutes, the catalyst temperature is 440° C. In 8 minutes, 0.320 part per hour of an off-gas from a different oxidative dehydrogenation of methanol over a silver catalyst, which gas contains 0.45 percent by volume of carbon monoxide, 4.5 percent by volume of carbon dioxide, 18.0 percent by volume of hydrogen and 0.05 percent by volume of formaldehyde, is fed into the starting mixture in the stream of gas and vapor, upstream from the catalyst.

The amount of air is then increased to 0.325 part per hour in the course of 0.25 hour, during which time, if the pressure is 1.07 bar, the catalyst temperature assumes a value of 700° C.

The throughput is then increased in the course of 52 hours to 2 tonnes of methanol per hour per square meter, at a constant catalyst temperature of 700° C, and at the same time the throughput of steam, air and off-gas is raised gradually in the corresponding ratio; the reaction is then carried out for 120 days at this final level of throughput. The pressure rises, during this time, from 1.20 bars to 1.56 bars. On reaching the final level of throughput, the amounts per hour are 14.29 parts of air, 1.57 parts of steam, 6.28 parts of methanol and 7.07 parts of off-gas. The reaction mixture is cooled continuously to 150° C and then absorbed, after further cooling, in water in an absorption tower. From the 52nd hour onward, 5.205 tonnes per hour of formaldehyde (taken as 100% strength) are obtained in the form of a 50.2 percent strength by weight aqueous solution containing 1.05% by weight of methanol and 0.009% by weight of formic acid. This corresponds to a yield of 89.93% of theory and to 98.26% conversion. The yield of end product and the methanol content of the formaldehyde solution obtained remain constant for 120 days. No cracks form in the catalyst bed.

EXAMPLE 3

An installation using a methanol vaporizer and a vertical reactor is used. At its top, the reactor is fitted with the inlet for the starting mixture, which is in the vapor state, and with the reactor hood. The catalyst bed is below the reactor top and a cooling zone is provided lower still. The reactor is coupled to an absorption column.

A catalyst comprising 0.187 part of silver crystals of the following composition is introduced into the reactor:

|  | Proportion in the catalyst (% by weight) | Particle sizes mm |
|---|---|---|
| Layer 1 | 12.9 | 0.4 – 0.75 |
| Layer 2 | 1.2 | 0.2 – 0.4 |
| Layer 3 | 5.3 | 0.75 – 1 |
| Layer 4 | 14.1 | 1 – 1.75 |
| Layer 5 | 66.5 | 1 – 2.5 |

Layer 2 is sprinkled as an annular layer onto layer 3, in the edge zone of the catalyst. The catalyst bed diameter is 200 cm and the internal diameter of the annular layer is 197 cm.

The catalyst is heated to 330° C by passing hot nitrogen through it.

The vapors, at a temperature of 74° C, issuing from a vaporizer and consisting of 0.18 part of methanol and 0.12 part of steam per hour enter the hood of the reactor and flow through the catalyst. The nitrogen feed is discontinued. The throughput is 0.057 tonne of methanol per square meter of catalyst bed cross-section per hour.

0.15 part of air per hour is now passed into the liquid in the vaporizer, whereupon the temperature of the catalyst begins to rise. After 2 minutes, the catalyst temperature is 440° C. In 5 minutes, 7.1 parts per hour of an off-gas from the same oxidative dehydrogenation of methanol over a silver catalyst, which gas contains 0.38 percent by volume of carbon monoxide, 4.7 percent by volume of carbon dioxide, 16.6 percent by volume of hydrogen and 0.04 percent by volume of formaldehyde, is fed into the starting mixture in the stream of gas and vapor, upstream from the catalyst.

The amount of air is then increased to 0.400 part per hour in the course of 1 hour, during which time, if the pressure is 1.10 bars, the catalyst temperature assumes a value of 700° C.

The throughput is then increased in the course of 55 hours to 2 tonnes of methanol per hour per square meter, at a constant catalyst temperature of 700° C, and at the same time the throughput of steam, air and off-gas is raised gradually in the corresponding ratio; the reaction is then carried out for 120 days at this final level of throughput. The pressure rises, during this time, from 1.25 to 1.55 bars. On reaching the final level of throughput, the amounts per hour are 14.3 parts of air, 1.57 parts of steam, 6.28 parts of methanol and 7.1 parts of off-gas. The reaction mixture is cooled continuously to 150° C and then absorbed, after further cooling, in water in an absorption tower. From the 55th hour onward, 5.200 tonnes per hour of formaldehyde (taken as 100% strength) are obtained in the form of a 50.5 percent strength by weight aqueous solution containing 1.10% by weight of methanol and 0.010% by weight of formic acid. This corresponds to a yield of 89.9% of theory and to 98.2% conversion. The yield of end product and the methanol content of the formaldehyde solution obtained remain constant for 120 days. No cracks form in the catalyst bed.

We claim:

1. In a process for the manufacture of formaldehyde by oxidative dehydrogenation of methanol in the presence of a silver catalyst, at an elevated temperature, the improvement wherein the reaction is started at a lower throughput and a lower temperature comprising
   (a) a gaseous starting mixture consisting of methanol and steam, containing from 0.1 to 0.7 mole of water per mole of methanol, is passed through a catalyst bed of silver particles, heated to from 250 to 450° C, at a throughput of from 0.04 to 1.0 tonne of methanol per square meter of catalyst bed cross-section per hour, thereafter
   (b) air corresponding to from 0.3 to 0.6 mole of oxygen per mole of methanol is thereafter added to the starting mixture at the above temperature, and the silver-catalyzed reaction is started,
   (c) at a point in time ranging from just after the start of said reaction to 0.5 hour after the start of said reaction, an off-gas taken from the same or another process for manufacture of formaldehyde by oxidative dehydrogenation of methanol and containing from 0.25 to 1.0 percent by volume of carbon monoxide, from 3.5 to 10 percent by volume of carbon dioxide, from 10 to 25 percent by volume of hydrogen and from 0.02 to 0.1 percent by volume of formaldehyde vapor, is admixed with the starting mixture, in amounts of from 90 to 3,500% by weight of off-gas, based on methanol, and is passed therewith through said catalyst bed,
   (d) the throughput of gaseous mixture fed to the catalyst, and the reaction temperature, are both increased and finally
   (e) the oxidative dehydrogenation reaction is carried out at from 550° to 800° C, at a throughput of from 1 to 3 tonnes of methanol per square meter of catalyst bed cross-section per hour, using from 0.2 to 0.7 mole of steam and from 0.3 to 0.8 mole of oxygen per mole of methanol, and from 90 to 180% by weight of off-gas, based on methanol.

2. A process as claimed in claim 1, wherein the catalyst is heated to from 280° to 350° C before starting stage (a) of the process and the starting mixture is then passed through the catalyst bed, using from 0.3 to 0.5 mole of steam per mole of methanol vapor, at a throughput of from 0.05 to 0.7 tonne of methanol per square meter of catalyst bed cross-section per hour.

3. A process as claimed in claim 1, wherein the starting mixture, in the vapor state, is at from 60° to 85° C before entering the catalyst bed.

4. A process as claimed in claim 1, wherein the air is fed continuously into the starting mixture which is in the vapor state, using from 0.35 to 0.45 mole of oxygen, in the form of air, per mole of methanol.

5. A process as claimed in claim 1, wherein the starting mixture is passed through the catalyst bed for from 0.1 to 120 minutes, and the air is then admixed therewith.

6. A process as claimed in claim 1, wherein the off-gas contains from 0.4 to 0.7 percent by volume of carbon monoxide, from 4.5 to 7 percent by volume of $CO_2$, from 15 to 22 percent by volume of $H_2$ and from 0.03 to 0.07 percent by volume of formaldehyde.

7. A process as claimed in claim 1, wherein the off-gas is admixed with said starting mixture within 0.25 hour from the start of the oxidative dehydrogenation reaction.

8. A process as claimed in claim 1, wherein from 105 to 3,200% by weight of off-gas, based on methanol, is used.

9. A process as claimed in claim 1 wherein, after the start of the reaction, the temperature is raised continuously in the course of 10 to 150 minutes, at from 1° to 30° C per minute, to from 650° to 800° C.

10. A process as claimed in claim 1, wherein from 0.3 to 0.5 mole of steam and from 0.4 to 0.6 mole of oxygen in the form of air are used per mole of methanol, from 105 to 158% by weight, based on methanol, of off-gas is employed, and the throughput is from 1.25 to 2.1 tonnes of methanol per square meter of catalyst bed cross-section per hour.

11. A process as claimed in claim 1, wherein stages (a) and (b) are carried out for from 2 to 30 minutes, the catalyst is then heated in the course of from 10 to 150 minutes, and for the remainder of the reaction time the starting mixture is reacted as in process stage (e).

12. A process as claimed in claim 1, wherein pressures of from 0.5 to 2 atmospheres are used.

* * * * *